(12) United States Patent
Skranc et al.

(10) Patent No.: US 12,134,589 B2
(45) Date of Patent: Nov. 5, 2024

(54) PROCESS FOR THE PRODUCTION OF SUBSTITUTED 2-[2-(PHENYL) ETHYLAMINOJALKANEAMIDE DERIVATIVES

(71) Applicant: Newron Pharmaceuticals S.p.A., Bresso (IT)

(72) Inventors: Wolfgang Skranc, Vienna (AT); Michael Wolberg, Neutraubling (DE); Matthias Riepl, Altenhann (DE); Christoph Imboden, Hofstetten Solothurn (CH); Erwin Waldvogel, Aesch (CH)

(73) Assignee: Newron Pharmaceuticals S.p.A., Bresso (IT)

( * ) Notice: Subject to any disclaimer, the term of this patent is extended or adjusted under 35 U.S.C. 154(b) by 504 days.

(21) Appl. No.: 17/603,454

(22) PCT Filed: Apr. 8, 2020

(86) PCT No.: PCT/EP2020/060037
§ 371 (c)(1),
(2) Date: Oct. 13, 2021

(87) PCT Pub. No.: WO2020/212227
PCT Pub. Date: Oct. 22, 2020

(65) Prior Publication Data
US 2022/0177417 A1    Jun. 9, 2022

(30) Foreign Application Priority Data
Apr. 17, 2019 (EP) ..................... 19169714

(51) Int. Cl.
*C07C 231/12* (2006.01)
(52) U.S. Cl.
CPC .................... *C07C 231/12* (2013.01)
(58) Field of Classification Search
None
See application file for complete search history.

(56) References Cited

U.S. PATENT DOCUMENTS

2008/0319057 A1* 12/2008 Thaler .................. C07D 213/38
514/471

FOREIGN PATENT DOCUMENTS

| CN | 1585743 A | 2/2005 |
|---|---|---|
| JP | H02180857 A | 7/1990 |
| JP | 2002105047 A | 4/2002 |
| JP | 2005509026 A | 4/2005 |
| JP | 2009530344 A | 8/2009 |
| JP | 2010529969 A | 9/2010 |
| JP | 2012219074 A | 11/2012 |
| WO | 2005047251 A1 | 5/2005 |
| WO | 2007071311 A1 | 6/2007 |
| WO | 2013133419 A1 | 9/2013 |
| WO | 2015004075 A1 | 1/2015 |

OTHER PUBLICATIONS

MacAllister M I et al., "The hydrogenation of mandelonitrile over a Pd/C catalyst: towards a mechanistic understanding", RCS Adv 2019 9, 26116-26125.
Office Action issued on counterpart Indian Patent Application No. 202117051958 on Jul. 19, 2023.
Raj IV P et al., "A facile direction conversion of aldehydes to esters and amides using acetone cyanohydrin", Tetrahedron Letters, 46 (2005) 8303-8306.
Jiang et al. "Pyrrolidinones as potent functional antagonists of the human melanocortin-4-receptor", Bioorganic & Medicinal Chemistry Letters, Pergamon, Amsterdam, NL, vol. 17, No. 20, Sep. 14, 2007, pp. 5610-5613.
Search Report and Written Opinion of PCT/EP2020/060037 of Jul. 21, 2020.
Adachi J et al., "The syntheses of 2,5-dihydroxypyrazines and their derivatives", J Heterocyclic Chem., 23, 871 (1986).
Office Action issued Dec. 14, 2023 in counterpart Chinese Patent Application No. 202080029134.X.
Effenberg F, "Synthesis and reactions of optically active cynohydrins", Angew. Chem. Ints. Ed. Engl. 1994, 33, 1555-1564.
Office Action issued Feb. 6, 2024 in connection with counterpart Japanese Patent Application No. 2021-560987.

(Continued)

*Primary Examiner* — Sudhakar Katakam
*Assistant Examiner* — Jennifer C Sawyer
(74) *Attorney, Agent, or Firm* — Silvia Salvadori, P.C.; Silvia Salvadori

(57) ABSTRACT

The present invention relates to a new process for the production of substituted 2-[2-(phenyl) ethylaminojalkaneamide derivatives of the following formula (I), in particular 2-[2-(3-butoxyphenyl)-ethylamino]-N,N-dimethylacetamide in high yields with very high chemical purity. The invention relates to a process for preparing a compound of formula (I) or a pharmaceutically acceptable salt thereof:

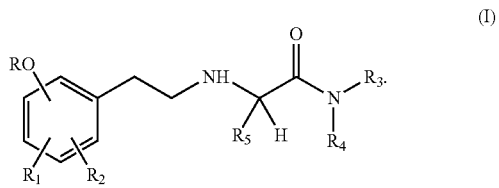

17 Claims, 1 Drawing Sheet

(Continued)

(56) References Cited

OTHER PUBLICATIONS

Office action issued on Feb. 8, 2024 in connection with Indian patent application No. 202117051958.
Veum L et al., "Catalytic hydrogenation of Cynohydrin esters as a novel approach to N-Acylated beta-amino alcohols—reaction optimisation by a design of experimental approach", Eur. J. Org. Chem. 2006, 1664-1671.

* cited by examiner

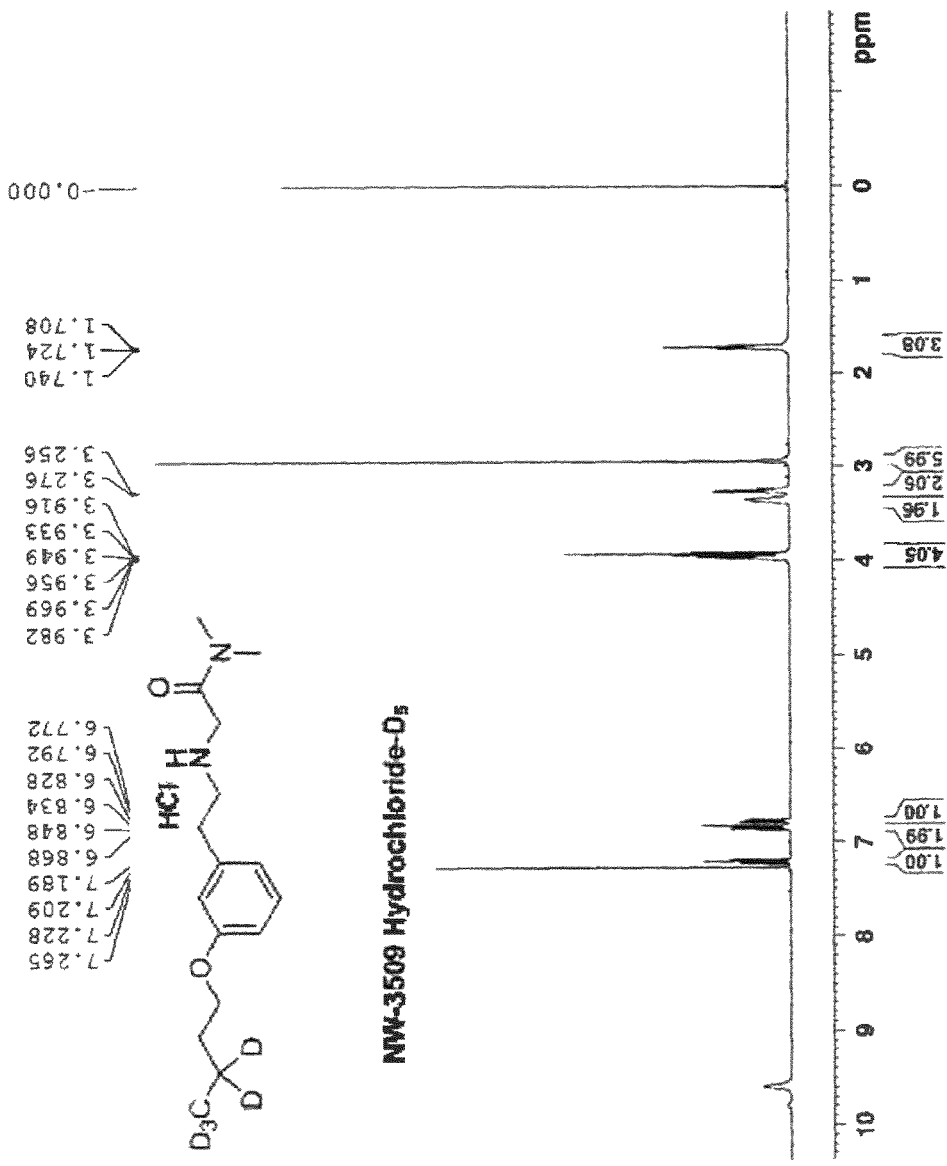

PROCESS FOR THE PRODUCTION OF SUBSTITUTED 2-[2-(PHENYL) ETHYLAMINO]ALKANEAMIDE DERIVATIVES

This application is a U.S. national stage of PCT/EP2020/060037 filed on 8 Apr. 2020, which claims priority to and the benefit of European Application No. 19169714.3 filed on 17 Apr. 2019, the contents of which are incorporated herein by reference in their entireties.

The present invention relates to a new process for the production of substituted 2-[2-(phenyl) ethylamino]alkaneamide derivatives, in particular 2-[2-(3-butoxyphenyl)-ethylamino]-N,N-dimethylacetamide in high yields with very high chemical purity.

BACKGROUND OF THE INVENTION

Substituted 2-[2-(phenyl) ethylamino]alkaneamide derivatives, disclosed in WO 2008/151702, are sodium and/or calcium channel modulators and therefore are useful in preventing, alleviating and curing a wide range of pathologies where said mechanisms play a pathological role, such as neurological, cognitive, psychiatric, inflammatory, urogenital and gastrointestinal diseases. These compounds are also described to be substantially free of monoamine oxidase (MAO) inhibitory effect.

A new class of fluorinated arylalkylamino carboxamide derivatives which are highly potent as sodium and/or calcium channel modulator are disclosed in WO 2013/000651.

WO 2008/151702 discloses in the examples the synthesis of 2-[2-(3-butoxyphenyl)-ethylamino]-N,N-dimethylacetamide hydrochloride, as summarized in the following Scheme 1:

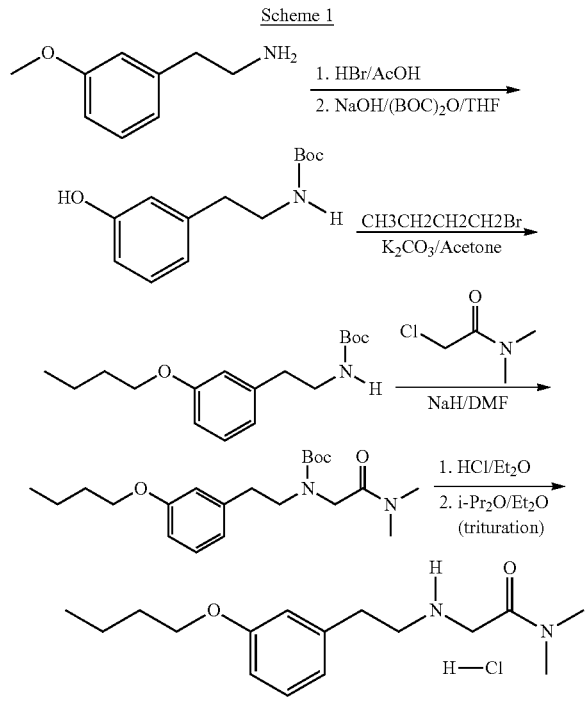

The disclosed process suffers of many drawbacks which make it not scalable at an industrial level:

- non commercially available starting material such as 3-methoxyphenylethyl amine, which preparation from commercially available reagents involves a couple of steps;
- difficult purifications of intermediates as they are oils;
- use of toxic reagents in large excess, such as 1-bromobutane and 2-chloro-N,N-dimethylacetamide, which is potentially genotoxic;
- use of non-standard equipment (NaH/DMF is a potentially explosive compound as $H_2$ is generated in the reaction);
- non practical and potentially very dangerous conditions for producing the final hydrochloride due to the use of ethereal solvents which easily form peroxides in the presence of air;
- low overall yields (about 13%);
- unknown purity of the final product.

BRIEF DESCRIPTION OF THE DRAWINGS

FIG. 1 shows the $^1$HNMR-spectrum of 2-[2-(3-butoxy-3,3,4,4,4-$d_5$-phenyl)-ethylamino]-N,N-dimethylacetamide hydrochloride.

DESCRIPTION OF THE INVENTION

The present invention relates to a process for preparing a compound of formula (I) or a pharmaceutically acceptable salt thereof:

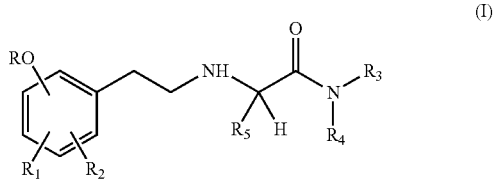

wherein R is $(C_3-C_{10})$alkyl, or ω-trifluoro$(C_3-C_{10})$alkyl;
$R_1$ and $R_2$ are, independently, hydrogen, hydroxy, $(C_1-C_8)$alkoxy, $(C_1-C_8)$ alkylthio, halo, trifluoromethyl or 2,2,2-trifluoroethyl; or one of $R_1$ and $R_2$ is at the ortho position to the R—O— group and, taken together with the same R—O—, represents a

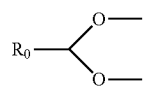

group where $R_0$ is $(C_2-C_9)$alkyl;
$R_3$ and $R_4$ are independently hydrogen or $(C_1-C_6)$alkyl; or taken together with the adjacent nitrogen atom form a 5-6 membered monocyclic saturated heterocycle, optionally containing one additional heteroatom chosen among —O—, —S— and —$NR_7$— where $R_7$ is hydrogen or $(C_1-C_6)$ alkyl;
$R_5$ is hydrogen or $(C_1-C_6)$alkyl;
and wherein optionally one or more hydrogen atom in the groups R, $R_1$, $R_2$, $R_3$, $R_4$ and $R_5$, preferably in the R group, can be substituted by a deuterium atom;

said process comprising the steps of
i) reacting a compound of formula (II) or a salt thereof

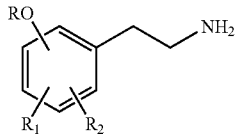
(II)

wherein R, $R_1$, $R_2$, are as above defined, with a compound of formula (III):

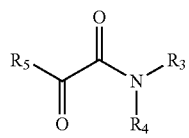
(III)

wherein $R_3$, $R_4$ and $R_5$ are as above defined, under reducing conditions, to obtain the compound of formula (I) as above defined, and
ii) optionally salifying the obtained compound of formula (I).

Preferably the compound of formula (II) is in the form of a salt with an acid selected from hydrochloric acid, benzenesulfonic acid, hydrobromic acid camphorsulfonic acid, methanesulfonic acid, ethanesulfonic acid, fumaric acid, lactic acid, maleic acid, mandelic acid, sulfuric acid, tartaric acid, succinic acid, paratoluenesulfonic acid and 2-naphtalenesulfonic acid.

A preferred process of the invention is the above described process for obtaining a compound of formula (I'):

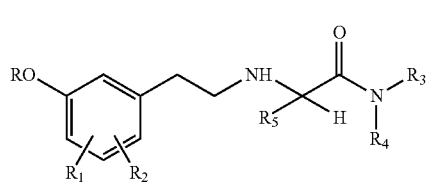
(I')

wherein R, $R_1$, $R_2$, $R_3$, $R_4$ and $R_5$ are as defined above and the compound of formula (II) has the following formula (II'):

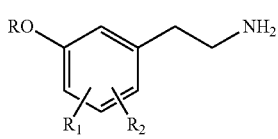
(II')

In specific embodiment, the present invention is directed to a hydrochloride salt of a substituted arylethylamino compounds, wherein said compound has the formula (I) or (I').

A preferred process of the invention is the above described process for obtaining a compound of formula (I) or (I') wherein:

R is $(C_4-C_6)$alkyl or $CD_3$-$CD_2$-$(C_3-C_4)$alkyl;
$R_1$ and $R_2$ are, independently, hydrogen or halo, preferably fluoro;
$R_3$ and $R_4$ are, independently, hydrogen or $(C_1-C_3)$alkyl;
$R_5$ is hydrogen or $(C_1-C_3)$alkyl.

A most preferred process of the invention is the above defined process for obtaining a compound of formula (I) or (I') as above defined wherein R is n-butyl or $CD_3$-$CD_2$-$CH_2$—$CH_2$— and $R_1$, $R_2$, $R_3$, $R_4$ and $R_5$, are hydrogen.

Step i) may be carried out under conditions of catalytic hydrogenation by using a heterogeneous catalyst selected from the group consisting of a catalyst comprising at least one metal from the list of Pd, Pt, Ir, Ni and Ru catalysts, such as a palladium or platinum catalyst, on an inert support in solvent at a pH from 9.0 to 10.5.

The solvent is selected from the group consisting of water, alcohols, ethers.

Preferably the catalyst is wet 5% Pt/C (50% $H_2O$) or wet 10% Pd/C (50% $H_2O$), preferably wet 10% Pd/C (50% $H_2O$).

The process is carried out at a hydrogen pressure comprised between 1 and 4 Atm preferably between 2.5 and 3.5 Atm and at a temperature comprised 0° C. and 10° C., preferably between 0° C. and 5° C.

Step ii) (salt formation) can be carried out by reacting the compound of Formula (I) or (I') with an acid in an appropriate solvent. Preferably the acid is selected from hydrochloric acid, benzenesulfonic acid, hydrobromic acid, camphorsulfonic acid, methanesulfonic acid, ethanesulfonic acid, fumaric acid, lactic acid, maleic acid, mandelic acid, sulfuric acid, tartaric acid, succinic acid, paratoluenesulfonic acid and 2-naphtalenesulfonic acid.

Most preferably the acid is hydrochloric acid.

Suitable solvents can be methanol, ethanol, isopropanol, acetone, methyl ethyl ketone and methyl isobutyl ketone, methyl isobutyl ketone is preferred.

The compound of formula (III) may be obtained in situ by hydrolysis of a compound of formula (VII):

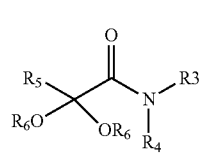
(VII)

wherein $R_3$, $R_4$ and $R_5$ are as defined above and $R_6$ is a $(C_1-C_4)$alkyl, preferably methyl, ethyl, iso-propyl.

The hydrolysis reaction is preferably carried out in water in the presence of an acid such as hydrochloric acid, hydrobromic acid, sulfuric acid, and phosphoric acid at a temperature ranging from 25° C. and 70° C.

The compound of formula (II), wherein R, $R_1$ and $R_2$ are as above defined may be obtained by a process comprising the following steps:
i') reacting a compound of formula (IV):

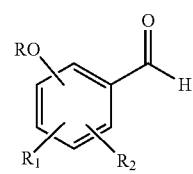
(IV)

wherein R, $R_1$, $R_2$, are as defined above, with MCN wherein M is an alkali metal chosen from Li, Na and K, to obtain a compound of formula (V):

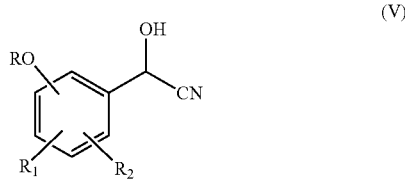

wherein R, $R_1$ and $R_2$ are as above defined, and ii') reducing the obtained compound of formula (V) to obtain a compound of formula (II) as above defined and iii') optionally salifying the obtained compound of formula (II).

The salt of the compound of formula (II) may be isolated by crystallization or directly used in the step i) described above.

Step i') is preferably carried out in a biphasic system consisting of water and an organic solvent in the presence of an acid at a temperature ranging from 0° C. to 10° C., preferably from 0° C. to 5° C.

The organic solvent is selected from the group consisting of tert-butyl methyl ether, 2-methytetrahydrofuran, toluene and the acid is selected from the group consisting of hydrochloric acid, sulfuric acid and phosphoric acid.

The reducing step ii') is preferably a catalytic hydrogenation which is preferably carried out by using an heterogeneous catalyst selected from the group consisting of nickel, rhodium, platinum and palladium catalysts on an inert support in a solvent selected from a lower aliphatic ($C_1$-$C_5$) alkanols such as methanol, ethanol, and isopropanol, tetrahydrofuran, 2-methytetrahydrofuran, ethyl acetate, isopropyl acetate, butyl acetate, toluene and heptanes and in the presence of an acid such as hydrochloric acid, sulphuric acid and phosphoric acid. In the present invention, reduction in methanol catalyzed by sulfuric acid is preferred.

The heterogeneous catalyst is preferably palladium or platinum catalyst such as wet 5% Pt/C (50% $H_2O$) or wet 10% Pd/C (50% $H_2O$), most preferably wet 10% Pd/C (50% $H_2O$).

Step ii') is preferably carried out at hydrogen pressure comprised between 0.5 and 4 Atm preferably between 2.5 and 3.5 Atm and the temperature is comprised between 30° C. and 90° C., preferably between 40° C. and 80° C.

The compound of formula (IV) as above defined may be obtained by alkylating a compound of formula (VI):

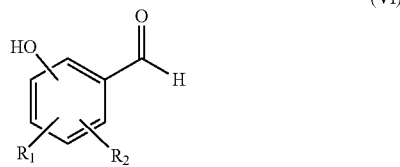

wherein $R_1$ and $R_2$ are as above defined with a compound of formula RX wherein R is as above defined and X is Cl, Br, I or a leaving group selected from the group consisting of mesylates, tosylates and brosylates.

The alkylation reaction is preferably carried out in aprotic polar solvents, such as acetonitrile, DMF, DMAC, DMSO, acetates such as ethyl acetate, isopropyl acetate, and n-butyl acetate in the presence of a inorganic base, such as potassium carbonate, sodium carbonate, cesium carbonate, at a temperature ranging from 15° C. to 120° C. Of the various combinations of solvents, bases, and temperatures, in DMF potassium carbonate at 110-120° C. is preferred. In alternative a preferred method for the alkylation is to carry out the reaction in two phase system consisting of an organic solvent, and an aqueous phase in the presence of a buffer and of a phase transfer catalyst.

The process according to the invention is scalable at industrial level without hazardous concerns. The overall molar yield is as high as 51%. Crystalline intermediate compound of formula (II) as hydrochloride allows recrystallization (if needed) ensuring that a high quality intermediate is used for the manufacture of the API.

The process involves commercially available materials.

EXPERIMENTAL PART

Synthesis of 2-[2-(3-butoxyphenyl)-ethylamino]-N,N-dimethylacetamide

2-[2-(3-Butoxyphenyl)-ethylamino]-N,N-dimethylacetamide was synthezised as reported in the following Scheme 2:

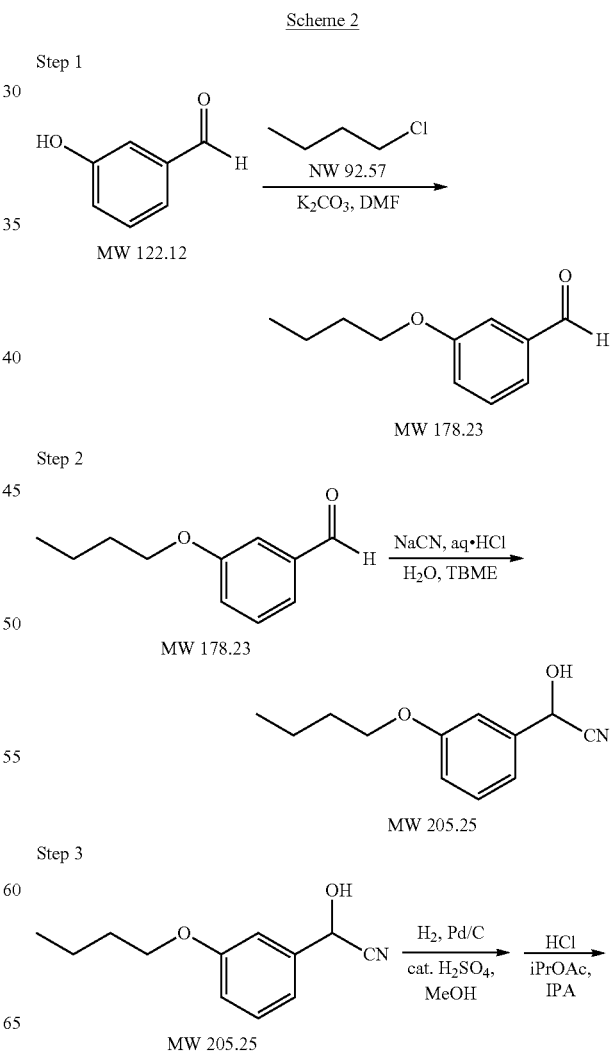

Step 4

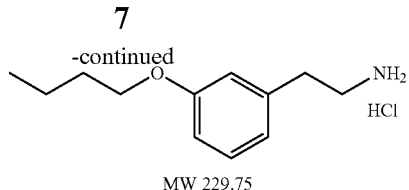

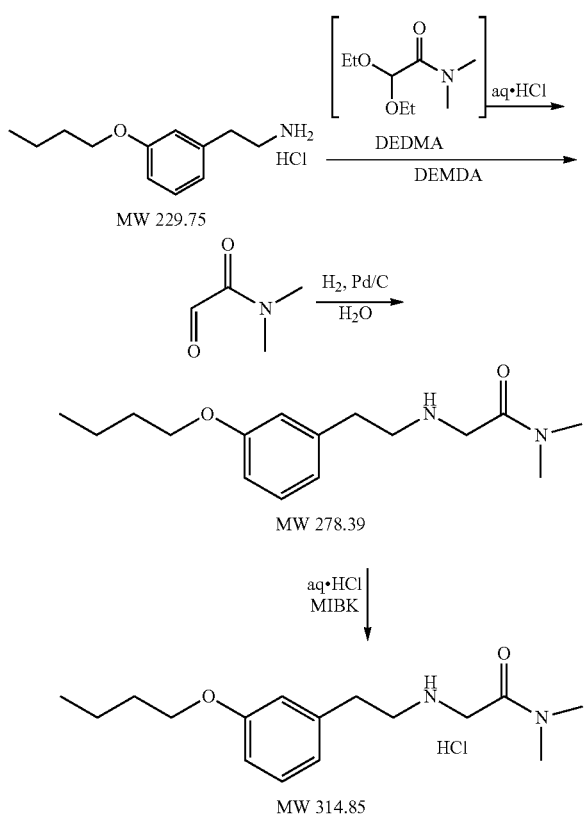

Example 1

Synthesis of 3-butoxybenzyaldehyde

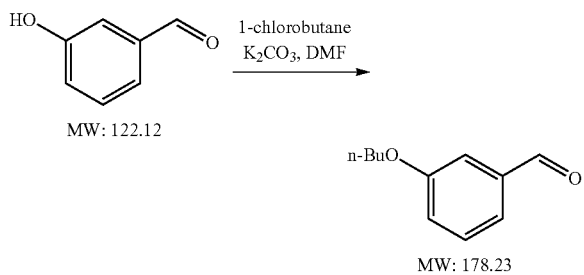

A mixture containing 3-hydroxybenzaldehyde 3.95 kg (32.34 mol), 1-chlorobutane 4.49 kg (48.52 mol), and potassium carbonate 6.26 kg (45.28 mol) in N,N-dimethylformamide 19.75 L was heated to 115-118° C. and kept at this temperature until the reaction was complete (3-hydroxybenzaldehyde circa 0.1% area %). The reaction mixture was cooled to circa 20° C. The slurry was added with a mixture of tert-butyl methyl ether 32.4 L and water 52.9 L and stirred for 15 min. The two phases mixture was allowed to separate. The organic solution was washed with a sodium chloride aqueous solution. The batch was concentrated under reduced pressure at <50° C. to provide the oily product 3-butoxybenzaldehyde 5.57 kg in 96.6% molar yield.

Example 2

Synthesis of 3-butoxybenzaldehyde

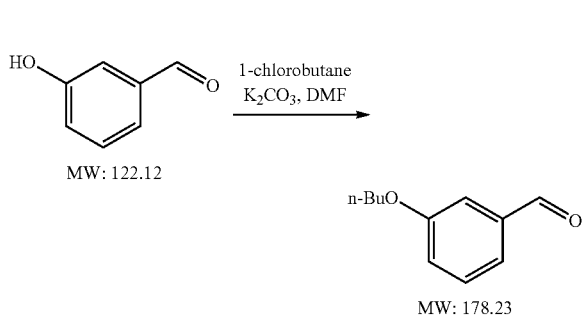

A solution containing 3-hydroxybenzaldehyde 25 kg (204.7 mol), potassium carbonate 39.5 kg (285.8 mol), and 1-chlorobutane 28.5 kg (307.8 mol) in N,N-dimethylformamide 120 kg was heated to 115° C. and kept at this temperature until reaction completion (3-hydroxybenzaldehyde less than 1%). The mixture was cooled, diluted with water 325 kg and then concentrated under vacuum to about 325 L. The batch was diluted with water 126 kg and methyl tert-butyl ether 150 kg was added at about 20° C. The aqueous layer was discarded and the batch was washed sequentially with dilute sodium chloride solution and then water. The batch was concentrated under vacuum and residual methyl tert-butyl ether was replaced by tetrahydrofuran through a series of dilution and concentration under vacuum. 33.5 kg (188.0 mol) of 3-butoxybenzaldehyde were obtained (91% molar yield, purity 99.7%).

MS (M+1: 179.1); $^1$H NMR is consistent with the given structure.

Example 3

Synthesis of Benzoacetonitrile,alpha-hydroxy-3-butoxy

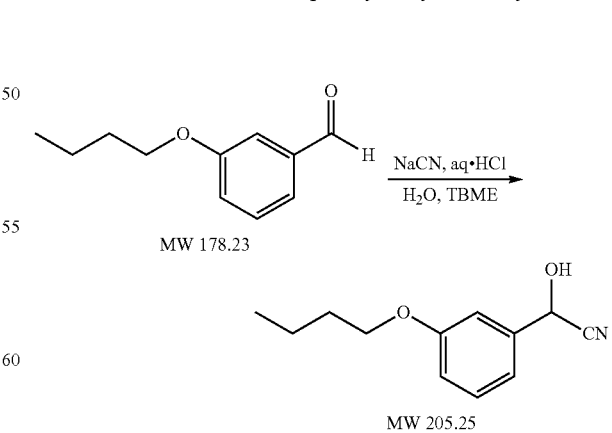

32% HCl 4.34 kg (38.11 mol) was added under stirring in 6 h to a two phases mixture, consisting of a solution of sodium cyanide 1.79 kg (36.53 mol) in water 4.18 L and of a solution of 3-butoxybenzaldehyde 5.43 kg (36.59 mol) in tert-butyl methyl ether (TBME) 7.94 L, at 0-5° C. The mixture was kept at 0-5° C. until the reaction was complete (Residual 3-butoxybenzaldehyde 2-3 wt % by $^1$H-NMR). The mixture was warmed to 18-25° C., and then diluted with tert-butyl methyl ether 11.5 L. The two phases were allowed to separate.

The organic solution was washed sequentially with water and then with a saturated sodium chloride aqueous solution. The organic solution was added to a solution of oxalic acid 0.027 kg in methanol 11.7 L. The solvent was replaced by methanol, by several cycles of dilution (with methanol) and the mixture concentrated under reduced pressure at <50° C., to give benzoacetonitrile,alpha-hydroxy-3-butoxy 6.16 kg (24.31 mol) 97% molar yield, as an oil.

Example 4

Synthesis of Benzeneethanamine, 3-butoxy Hydrochloride

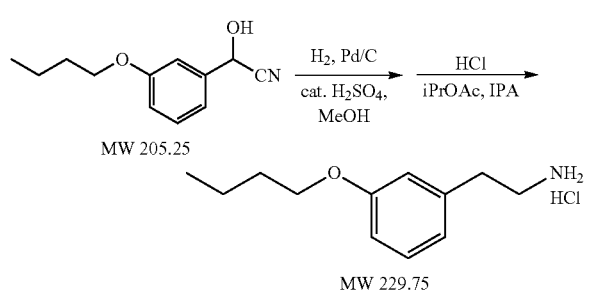

A mixture containing Benzoacetonitrile,alpha-hydroxy-3-butoxy 6.12 kg (29.82 mol), 10% Pd/C 0.31 kg; Evonik Type E196 NN/W; ~50% water wet, and 96% sulfuric acid 3.73 kg in methanol 51.5 L was stirred at 0-5° C. under hydrogen 0.5 bar. Then the reaction mixture was stirred at 40° C. under hydrogen 2 bar, and then at 80° C. under hydrogen 3 bar. The mixture was cooled to 20-25° C., purged with $N_2$ and diluted with water 22.5 L, the catalyst was removed by filtration and washed by water. The combined filtrate was concentrated at atmospheric pressure until the solution temperature reached about 90° C. (final volume ~31 L). The solution was extracted with a mixture of isopropyl acetate 6.12 L and heptanes 6.12 L. The aqueous layer was diluted with isopropyl acetate 43 L. Hyflo 1.22 kg was added. The pH of the aqueous solution was adjusted to pH 12-13 with a 50% solution of sodium hydroxide of about 3.64 kg. The mixture was filtered through a cellulose filter pad followed by isopropyl acetate washes. The combined filtrate (consisting of two phases) was allowed to separate and the aqueous layer was discarded. The organic phase was washed sequentially with 25% aqueous ammonium chloride 3.4 L and with brine. The batch was azeotropically dried under reduced pressure at max 50° C., filtered over cellulose filter pad and washed the pad with isopropyl acetate 6.12 L, and then the solution was concentrated to about 31 L at <50° C. A 5-6 M solution of hydrochloric acid in isopropanol 7.85 kg was added. The suspension was filtered at 0-5° C. with a rinse of cold isopropyl acetate (6.1 L). The wet product was dried under vacuum at 40° C. to give Benzeneethanamine, 3-butoxy hydrochloride 4.5 kg in 65.5% yield. Spectroscopic data (LC/MS, $^1$H NMR) were found to be consistent with the assigned structure of Benzeneethanamine, 3-butoxy hydrochloride.

LC/MS: [M-HCl+H]$^+$=194.2.

$^1$H NMR (400 MHz, DMSO-d$_6$); δ 8.17 (s, 3H), 7.24-7.20 (m, 1H), 6.83-6.79 (m, 3H), 3.97-3.94 (t, 2H), 3.04-2.99 (m, 2H), 2.89-2.85 (m, 2H), 1.72-1.65 (m, 2H), 1.48-1.39 (m, 2H), 0.95-0.92 (t, 3H).

Benzeneethanamine,3-butoxy hydrochloride 4.42 kg (19.24 mol) was further recrystallized from isopropanol 13.3 L, as described above, to provide highly pure Benzeneethanamine, 3-butoxy hydrochloride 3.99 kg in 90.3% yield.

Example 5

Synthesis of 2-[2-(3-butoxyphenyl)-ethylamino]-N,N-dimethylacetamide

Step 4

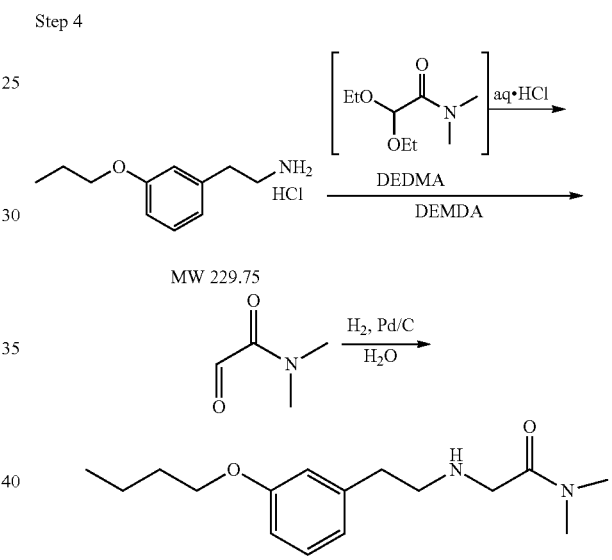

A solution of 32% aqueous hydrochloric acid 2.93 kg in water 23.16 kg was heated to 57° C.; 2,2-diethoxy-N,N-dimethylacetamide (DEDMA; 5.12 kg (29.23 mol) was added in two minutes to the acidic solution which was then kept under stirring at 58-61° C. for 60 min. (DEMDA 5.6% area %). The mixture was cooled to about 20° C., and added with 20% aqueous sodium hydroxide (about 5.48 kg) up to pH 8.8 and concentrated under vacuum at <45° C. to about 29 L residual volume.

The above solution was added to solid Benzeneethanamine, 3-butoxy hydrochloride 3.95 kg (17.19 mol) and the pH was adjusted to pH 9.9 at 19-20° C. with 20% aqueous sodium hydroxide, about 4.19 kg. Wet (1:1=water:Pd/C) 5% Pd/C 0.18 kg was added under stirring to the mixture that was then hydrogenated with $H_2$ (3 bar) at 0-5° C. until reaction is complete (Benzeneethanamine, 3-butoxy hydrochloride <0.2% areal. The mixture was diluted with water (circa 10 L) and neutralized with aqueous hydrochloric acid. The batch was filtered at 5-10° C., added under stirring with tert-butyl methyl ether 20.5 L, and the phases were separated. The aqueous layer was diluted with methyl isobutyl ketone 22.1 kg and the pH was adjusted to pH 9.8 with 50% aqueous sodium hydroxide, about 2.0 kg. The phases were allowed to separate and the aqueous phase was extracted with methyl isobutyl ketone 11.0 kg. Saturated sodium chloride aqueous solution 8.18 kg was added to the combined organic phases and the mixture was stirred for 5 minutes. The phases were allowed to separate after addition of water 3.20 kg.

Example 6

Synthesis of 2-[2-(3-butoxyphenyl)-ethylamino]-N,N-dimethylacetamide hydrochloride

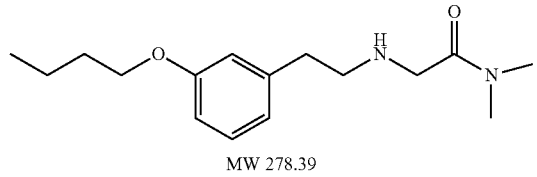

MW 278.39 aq·HCl
MIBK
↓

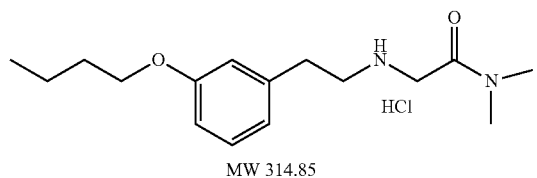

MW 314.85

A solution of 2-[2-(3-butoxyphenyl)-ethylamino]-N,N-dimethylacetamide free base 5.4 Kg in methyl isobutyl ketone solution 35 L was added to 37% hydrochloric acid 2.03 kg. The mixture was dried azeotropically by repeated cycles of dilution with methyl isobutyl ketone and then concentrated under vacuum at <45° C. to about 27 L residual volume. The precipitated solid was filtered, and was washed sequentially with methyl isobutyl ketone 10.95 kg and heptanes 18.70 kg. The wet product was dried at 40° C., to give 2-[2-(3-butoxyphenyl)-ethylamino]-N,N-dimethylacetamide hydrochloride salt 4.91 kg as a white solid in 90.7% yield. Spectral data ($^1$H NMR), of the solid is consistent with the assigned structure of 2-[2-(3-butoxyphenyl)-ethylamino]-N,N-dimethylacetamide hydrochloride. The identity of 2-[2-(3-butoxyphenyl)-ethylamino]-N,N-dimethylacetamide hydrochloride was confirmed by elemental analysis (theoretical vs found: C, 61.04% vs 61.3±0.2 wt %; H, 8.64% vs 8.7±0.1 wt %; N, 8.90% vs 8.9±0.1 wt %; O 10.16% vs 10.17±0.1 wt %; Cl 11.26% vs 10.2±0.5 wt %) (MS (M+1: 279.0), and 300 MHz $^1$H NMR Spectrum in DMSO Bruker Avance 300 at 20° C.:

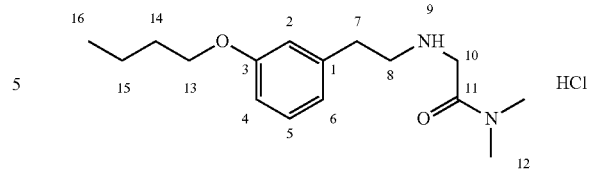

| Chemical Shift [ppm] | Multiplicity | Number of Hydrogen | Assignment |
|---|---|---|---|
| 0.94 | t | 3 | 16 (CH$_3$) |
| 1.35-1.53 | m | 2 | 15(CH$_2$) |
| 1.62-1.77 | m | 2 | 14 (CH$_2$) |
| 2.90 | s | 3 | 12a (CH$_3$) |
| 2.94 | s | 3 | 12b (CH$_3$) |
| 2.97-3.05 | m | 2 | 7 (CH$_2$) |
| 3.08-3.22 | m | 2 | 8 (CH$_2$) |
| 3.95 | t | 2 | 13 (CH$_2$) |
| 4.05 | s | 2 | 10 (CH$_2$) |
| 6.75-6.88 | m | 3 | 2 (CH), 4 (CH), 6 (CH) |
| 7.18-7.30 | m | 1 | 5 (CH) |
| 9.26 | bs | 2 | —NH$_2$$^+$— |

Bruker Avance 300 $^3$C-NMR Spectrum in DMSO at 20° C.

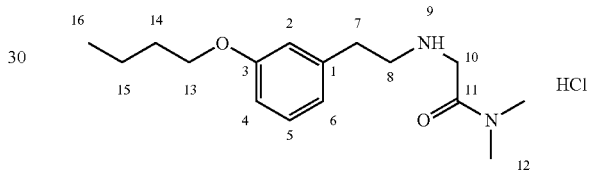

| Chemical Shift [ppm] | Kind of Carbon Atom | Assignment |
|---|---|---|
| 14.57 | CH$_3$ | 16 |
| 19.62 | CH$_2$ | 15 |
| 31.64 | CH$_2$ | 14 |
| 32.13 | CH$_2$ | 7 |
| 35.77 | CH$_3$ | 12a, b |
| 36.54 | CH$_3$ | |
| 47.67 | CH$_2$ | 10 |
| 48.68 | CH$_2$ | 8 |
| 67.85 | CH$_2$ | 13 |
| 113.53 | CH | |
| 115.57 | CH | 2, 4, 6 |
| 121.47 | CH | |
| 130.55 | CH | 5 |
| 139.70 | C | |
| 159.76 | C | 1, 3, 11 |
| 165.89 | C | |

Example 7

Synthesis of 2-[2-(3-butoxyphenyl)-ethylamino]-N,N-dimethylacetamide Hydrochloride 2-[2-(3-Butoxyphenyl)-ethylamino]-N,N-dimethylacetamide free base 8.10 g (1 equiv.) was dissolved in diethyl ether 15 mL. To this solution HCl in ether solvent 46 mL (2 mmol) was added and vigorously stirred. The residue formed was scratched at 0° C. to produce a white precipitate of crude 2-[2-(3-butoxyphenyl)-ethylamino]-N,N-dimethylacetamide hydrochloride. This precipitate was further purified by trituration in ethyl acetate (40 mL) to give 2-[2-(3-butoxyphenyl)-ethylamino]-N,N-dimethylacetamide hydrochloride (6.66 g, 72% yield).

Example 8

Synthesis of 2-[2-(3-butoxy-3,3,4,4,4-$d_5$-phenyl)-ethylamino]-N,N-dimethylacetamide Hydrochloride

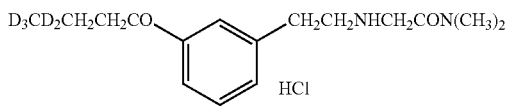

2-[2-(3-Butoxy-3,3,4,4,4-$d_5$-phenyl)-ethylamino]-N,N-dimethylacetamide free base 8.25 g (1 equiv.) was dissolved in diethyl ether 15 mL. To this solution HCl in ether solvent 46 mL (2 mmol) was added and vigorously stirred. The gummy residue formed was scratched at 0° C. to produce a white precipitate of crude 2-[2-(3-butoxy-3,3,4,4,4-$d_5$-phenyl)-ethylamino]-N,N-dimethylacetamide hydrochloride. This precipitate was further purified by trituration in ethyl acetate 40 mL. The resultant precipitate was filtered and dried under nitrogen to yield pure 2-[2-(3-butoxy-3,3,4,4,4-$d_5$-phenyl)-ethylamino]-N,N-dimethylacetamide hydrochloride 6.77 g, 72% yield.

$^1$HNMR-spectrum is reported in Figure 1;
LC-MS:

| m/z | Abundance |
|---|---|
| 283.30 | 4.5 |
| 284.30 | 100.0 |
| 285.30 | 12.7 |
| 286.30 | 1.8 |
| 305.80 | 0.5 |
| 306.25 | 7.1 |
| 307.25 | 0.8 |

2-[2-(3-Butoxy-3,3,4,4,4-$d_5$-phenyl)-ethylamino]-N,N-dimethylacetamide free base can be obtained according to the process described in examples 2, 3, 4 and 5 starting from 3-hydroxybenzaldehyde and using Butane-1,1,1,2,2-$d_5$-4-chloro instead of 1-chlorobutane.

The invention claimed is:

1. A process for preparing a compound of formula (I) or a pharmaceutically acceptable salt thereof:

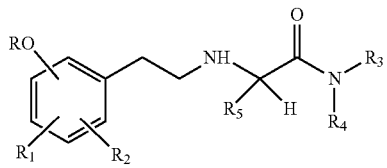

wherein R is ($C_3$-$C_{10}$)alkyl, or ω-trifluoro($C_3$-$C_{10}$)alkyl;
$R_1$ and $R_2$ are, independently, hydrogen, hydroxy, ($C_1$-$C_8$)alkoxy, ($C_1$-$C_8$) alkylthio, halo, trifluoromethyl or 2,2,2-trifluoroethyl; or one of $R_1$ and $R_2$ is at the ortho position to the R—O— group and, taken together with the same R—O—, represents a

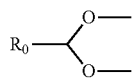

group where $R_0$ is ($C_2$-$C_9$)alkyl;
$R_3$ and $R_4$ are independently hydrogen or ($C_1$-$C_6$)alkyl; or taken together with the adjacent nitrogen atom form a 5-6 membered monocyclic saturated heterocycle, optionally containing one additional heteroatom chosen among —O—, —S— and —$NR_7$— where $R_7$ is hydrogen or ($C_1$-$C_6$) alkyl;
$R_5$ is hydrogen or ($C_1$-$C_6$)alkyl;
and wherein optionally one or more hydrogen atom in the groups R, $R_1$, $R_2$, $R_3$, $R_4$ and $R_5$ can be substituted by a deuterium atom;
said process comprising the steps of:
i) reacting a compound of formula (II) or a salt thereof

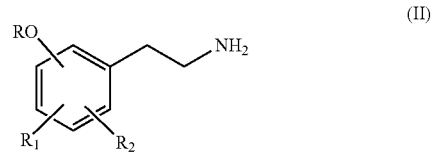

wherein R, $R_1$, $R_2$, are as above defined, with a compound of formula (III):

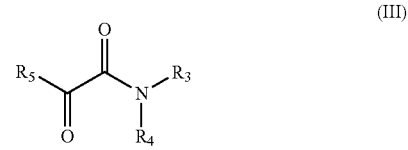

wherein $R_3$, $R_4$ and $R_5$ are as above defined, under reducing conditions, to obtain the compound of formula (I) as above defined, and
ii) optionally salifying the obtained compound of formula (I).

2. The process according to claim 1 for obtaining a compound of formula (I'):

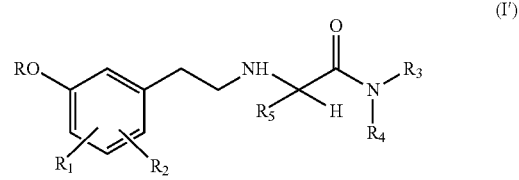

wherein R, $R_1$, $R_2$, $R_3$, $R_4$ and $R_5$ are as defined above and the compound of formula (II) has the following formula (II'):

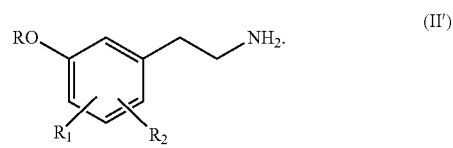

3. The process according to claim 1 for obtaining a compound of formula (I) or (I') wherein R is n-butyl or $CD_3$—$CD_2$—$CH_2$—$CH_2$— and $R_1$, $R_2$, $R_3$, $R_4$ and $R_5$ are hydrogen.

4. The process according to claim 1, wherein the compound of formula (II) is in the form of a salt with an acid selected from hydrochloric acid, benzenesulfonic acid, hydrobromic acid camphorsulfonic acid, methanesulfonic acid, ethanesulfonic acid, fumaric acid, lactic acid, maleic acid, mandelic acid, sulfuric acid, tartaric acid, succinic acid, paratoluenesulfonic acid and 2-naphtalenesulfonic acid.

5. The process according to claim 1, wherein step i) is carried out under conditions of catalytic hydrogenation.

6. The process according to claim 5 wherein the catalytic hydrogenation is carried out by using a catalyst comprising at least one metal selected from Pd, Pt, Ir, Ni and Ru on an inert support.

7. The process according to claim 6 wherein the catalytic hydrogenation is carried out wherein the catalyst is wet 5% Pt/C (50% $H_2O$) or wet 10% Pd/C (50% $H_2O$).

8. The process according to claim 1 wherein the compound of formula (III) is obtained in situ by hydrolysis of a compound of formula (VII):

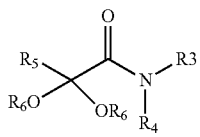

(VII)

wherein $R_3$, $R_4$ and $R_5$ are as defined above and $R_6$ is a ($C_1$-$C_4$)alkyl.

9. The process according to claim 1 wherein the compound of formula (II) as defined in claim 1, is obtained by a process comprising the following steps:

i') reacting a compound of formula (IV):

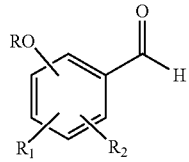

(IV)

wherein R, $R_1$, $R_2$, are as defined in claim 1, with MCN wherein M is an alkali metal chosen from Li, Na and K, to obtain a compound of formula (V):

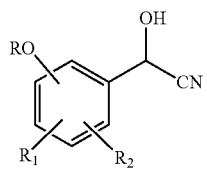

(V)

wherein R, $R_1$ and $R_2$ are as above defined, and ii') reducing the obtained compound of formula (V) to obtain a compound of formula (II) as above defined, and iii') optionally salifying the obtained compound of formula (II).

10. The process according to claim 9 wherein the salt of the compound of formula (II) may be isolated by crystallization or directly used in the step i) defined in claim 1.

11. The process according to claim 9 wherein step i') is carried out in a biphasic system consisting of water and an organic solvent in the presence of an acid at a temperature ranging from 0° C. to 10° C.

12. The process according to claim 9 wherein the reducing step ii') is preferably a catalytic hydrogenation which is carried out by using an heterogeneous catalyst selected from the group consisting of nickel, rhodium, platinum and palladium catalysts on an inert support.

13. The process according to claim 12 wherein the heterogeneous catalyst is wet 5% Pt/C (50% $H_2O$) or wet 10% Pd/C (50% $H_2O$).

14. The process according to claim 9 wherein the compound of formula (IV) as defined in claim 9 is obtained by alkylating a compound of formula (VI):

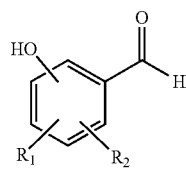

(VI)

wherein $R_1$ and $R_2$ are as defined in claim 1 with a compound of formula RX wherein R is as defined in claim 1 and X is Cl, Br, I or a leaving group selected from the group consisting of mesylates, tosylates and brosylates.

15. The process according to claim 1, wherein optionally one or more hydrogen atom in the groups R, $R_1$, $R_2$, $R_3$, $R_4$ and $R_5$ in the R group, is substituted by a deuterium atom.

16. The process according to claim 11 wherein step i') is carried out in in the presence of an acid at a temperature ranging from 0° C. to 5° C.

17. The process according to claim 13 wherein the heterogeneous catalyst is wet 5% Pt/C (50% $H_2O$).

* * * * *